(12) United States Patent
Sawada

(10) Patent No.: US 7,189,984 B2
(45) Date of Patent: Mar. 13, 2007

(54) OBJECT DATA INPUT APPARATUS AND OBJECT RECONSTRUCTION APPARATUS

(75) Inventor: Yasuhiro Sawada, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 68 days.

(21) Appl. No.: 11/151,883

(22) Filed: Jun. 13, 2005

(65) Prior Publication Data
US 2005/0274913 A1 Dec. 15, 2005

(30) Foreign Application Priority Data
Jun. 14, 2004 (JP) .............................. 2004-176200

(51) Int. Cl.
*G01N 21/86* (2006.01)
*G01B 11/24* (2006.01)
(52) U.S. Cl. ............................ 250/559.07; 250/559.22; 356/601
(58) Field of Classification Search ........... 250/559.05, 250/559.07, 559.22, 559.23; 356/425, 601, 356/326, 73
See application file for complete search history.

(56) References Cited

U.S. PATENT DOCUMENTS 6,469,788 B2 * 10/2002 Boyd et al. .................. 356/369
6,507,036 B1 * 1/2003 Godin ..................... 250/559.22
7,038,768 B2 * 5/2006 Takeuchi et al. .............. 356/73

FOREIGN PATENT DOCUMENTS

JP 5-187833 A 7/1993

OTHER PUBLICATIONS

Manabe, et al., "Simultaneous Measurement System of Spectral. . .", Trans. of the Institute of Electronics, Inform. and Comm. Engineers, vol. J86-D-II, No. 6, pp. 1012-1019, 2001.

* cited by examiner

Primary Examiner—Georgia Epps
Assistant Examiner—Don Williams
(74) Attorney, Agent, or Firm—Canon USA, Inc. Intellectual Property Division

(57) ABSTRACT

An apparatus providing a light-emitting unit for emitting a first light beam to an object and an imaging unit for capturing a first image representing the profile of the first light beam on the surface of the object and a second image representing the spectrum of the reflected first light beam.

4 Claims, 9 Drawing Sheets

LIGHT-SECTION IMAGE

SPECTRAL IMAGE

OBJECT DATA INPUT APPARATUS AND OBJECT RECONSTRUCTION APPARATUS

BACKGROUND OF THE INVENTION

1. Field of the Invention

The present invention generally relates to a technology for measuring the shape and the spectral reflectance of a real object and more particularly, but not exclusively, relates to a technology for measuring the three-dimensional shape of an object and the spectral reflectance corresponding to the three-dimensional shape.

2. Description of the Related Art

A conventional optical three-dimensional shape input apparatus, such as Kona Minolta's Vivid, includes, in addition to a shape measuring mechanism using a light section method, a charge-coupled device (CCD) color camera for obtaining shape data representing the shape of an object and a texture map representing the surface colors of the object. In this way, when shape of the object is reconstructed by computer graphics (CG) technology using the shape data, the colors and the patterns of the surface of the object can also be reconstructed.

Since a color camera is typically only capable of measuring colors using a group of images obtained through a limited number of color filters (usually, R, G, and B color filters), detailed spectral data cannot be obtained. Therefore, the colors recorded on the texture map only represent the colors under the lighting used when capturing the image. For this reason, the surface colors of the object observed under different lighting with a different spectrum cannot be reconstructed. Thus, the reconstructed image is not suitable for academic purposes, such as creating a digital archive and analyzing the composition of an art work.

Japanese Patent Laid-Open No. 05-187833 discloses a type of light section method for measuring the surface colors of an object using a plurality of single-wavelength laser beams as a slit beam. According to this method, the reflectance of a plurality of wavelengths can be measured. However, measurements, such as a spectral measurement, for contiguous spectral reflectance in a wide area are not possible.

An imaging spectrograph, such as the imaging spectrograph proposed in "Simultaneous Measurement System of Spectral Distribution and Shape" (Transactions of the Institute of Electronics, Information and Communication Engineers, Vol. J86-D-II, No. 6, pp 1012–1019, 2001) is used to obtain more detailed spectral data suitable for the usages described above.

However, an imaging spectrograph is typically only capable of capturing one vertically linear section at where the slit beam hits the surface of the object. Therefore, the method disclosed in Japanese Patent Laid-Open No. 05-187833 employs a pattern projection method for inputting the shape of the object. In this case, the object must be captured several times to obtain the shape data corresponding to the slit beam. Consequently, to obtain data for the entire periphery of the object, the object must be rotated by a small angle and the object is captured several times at each angle. As a result, capturing must be performed a numerous number of times.

SUMMARY OF THE INVENTION

At least one exemplary embodiment provides an object data input device including a light-emitting unit configured to emit a first light beam to an object, and an imaging unit configured to capture a first image representing the profile formed from a first portion of the first light beam reflected from the surface of the object and a second image representing the spectrum of a second portion of the first light beam reflected at the surface of the object. Where in some exemplary embodiments the first and second portions may not be equal.

At least one exemplary embodiment provides an object data generating device including a first processing unit configured to calculate the shape of an object based on a first image representing the profile formed from a reflected portion of a first light beam incident on the surface of the object, and a second processing unit configured to generate spectral data corresponding to the shape of the object based on the first image and a second image representing the spectrum of a portion of the first light beam reflected at the surface of the object.

At least one further exemplary embodiment provides an object data processing system including an object data input device and an object data generating device. The object data input device includes a light-emitting unit configured to emit a first light beam to an object and a imaging unit configured to capture a first image representing the profile formed from a reflected portion of the first light beam on the surface of the object and a second image representing the spectrum of a portion of the first light beam reflected at the surface of the object. In at least one exemplary embodiment, the object data generating device can include a first processing unit configured to calculate the shape of an object based on a first image representing the profile formed from a portion of the reflected light of a first beam of light incident on the surface of the object, and a second processing unit for generating spectral data corresponding to the shape of the object based on the first image and a second image representing the spectrum of a portion of the first light beam reflected at the surface of the object.

At least one exemplary embodiment provides an imaging apparatus including an optical member configured to guide an incident light beam to a first and second light path, and an image capturing unit configured to capture the first image presenting the profile of the incident light beam passing through the first light path and to capture the second image representing the spectrum of the incident light beam passing through the second light path.

At least one exemplary embodiment provides an imaging apparatus including a spectrographic unit configured to spectrographically separate an incident light beam, where in at least one exemplary embodiment the spectrographic unit is capable of moving into and out of the light path (e.g., the first light path and the second light path) of the incident light beam, and an image capturing unit configured to capture a first image representing the profile of the incident light beam while the spectrographic unit is moved out from the light path of the incident light beam and to capture a second image representing the spectrum of the incident light beam while the spectrographic unit is moved into the light path of the incident light beam.

At least one exemplary embodiment provides a method for inputting three-dimensional data including the steps of emitting a first light beam to an object and capturing a first image representing the profile formed from a reflected portion of the first light beam incident on the surface of the object and a second image representing the spectrum of the first light beam reflected at the surface of the object. Note that in at least one further exemplary embodiment no light need emitted by the exemplary embodiment, the light detected could be ambient or other light (e.g. daylight, detached light beam) incident on the object or even light emitted from the object (e.g. infrared).

At least one exemplary embodiment provides a method for generating object data including the steps of calculating the shape of an object based on a first image representing the profile formed from a reflected portion of the first light beam incident on the surface of the object and generating spectral data corresponding to the shape of the object based on the first image and a second image representing the spectrum of a portion of the first light beam reflected at the surface of the object.

At least one exemplary embodiment provides an object data processing program including a program code for controlling a computer to carry out the steps included in the method for inputting three-dimensional data according to an aspect of the present invention.

Further areas of applicability of exemplary embodiments will become apparent from the detailed description provided hereinafter. It should be understood that the detailed description and specific examples, while indicating exemplary embodiments, are intended for purposes of illustration only and are not intended to limit the scope of exemplary embodiments.

BRIEF DESCRIPTION OF THE DRAWINGS

Exemplary embodiments will become apparent from the following detailed description, taken in conjunction with the drawings.

DESCRIPTION OF THE EMBODIMENTS

The following description of exemplary embodiment(s) is merely illustrative in nature and is in no way intended to limit the invention, its application, or uses.

Processes, techniques, apparatus, and materials as known by one of ordinary skill in the art may not be discussed in detail but are intended to be part of the enabling description where appropriate. For example an optical element that can separate the frequency of incident light (e.g., prism) can be used to wavelength separate an incident light for spectral imaging and any material that can be used to form such an optical element should fall within the scope of exemplary embodiments (e.g., glass, Si).

Additionally the actual size of optical elements may not be discussed however any size from macro to micro and nano optical elements are intended to lie within the scope of exemplary embodiments (e.g., optical elements with characteristic sizes of nanometer size, micro size, centimeter, and meter sizes).

Additionally exemplary embodiments are not limited to visual optical systems, for example the system can be designed for use with infrared and other wavelengths systems. For example a light detector (e.g., a detector measuring E and B fields, or E fields, equivalents and any other light detector that can provide the information to produce a spectral image as known by one of ordinary relevant skill) can be used and the spectral image obtain computationally.

At least one exemplary embodiment, described below, provides apparatuses and systems for obtaining detailed spectral data of an object by carrying out imaging spectrography and a light section method. In at least one further exemplary embodiment, the image spectrograph uses the similar portion of light, with a similar number of cycles of measurement, as the light section method is used to measure the shape of the object.

Now, at least one exemplary embodiment will be described with reference to the drawings below.

First Embodiment

Figure 1:
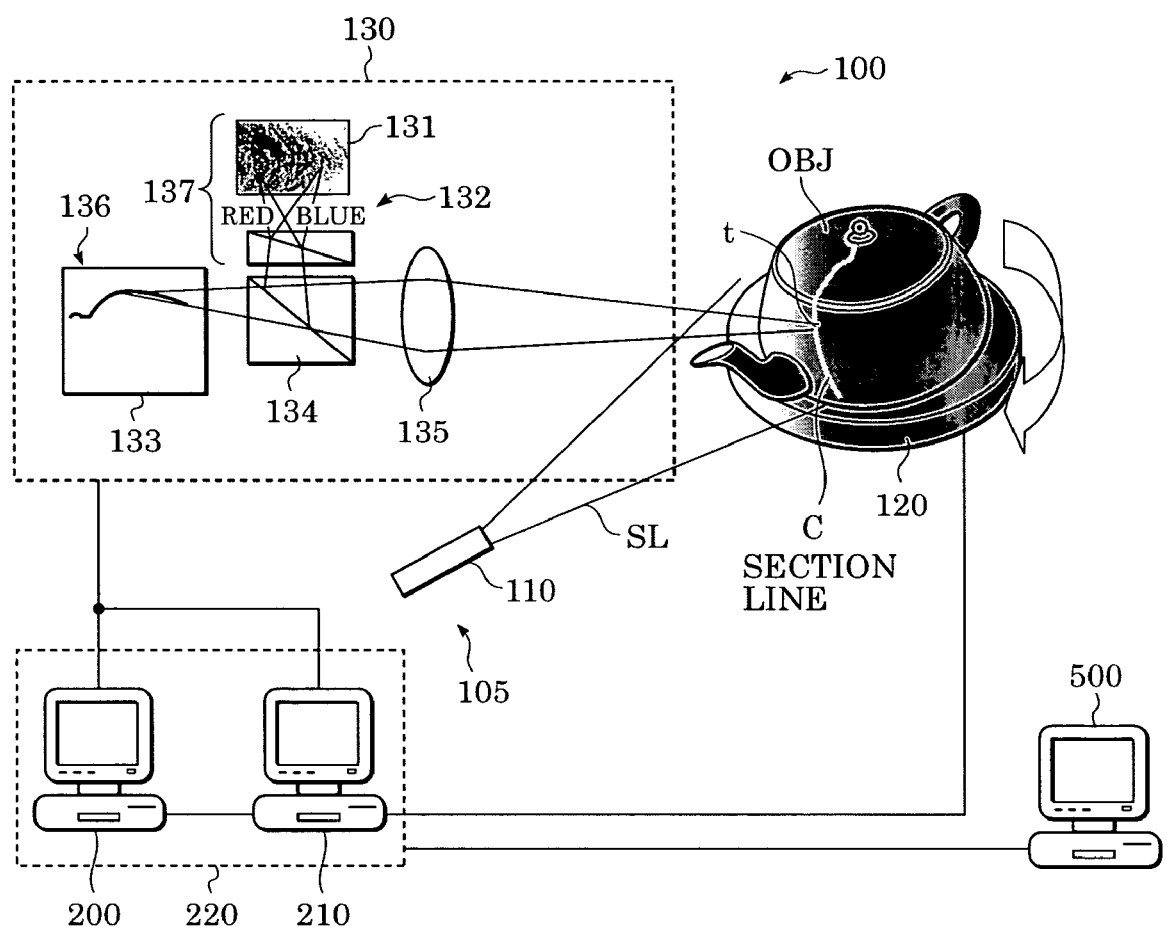
FIG. 1 illustrates the structure of a three-dimensional data processing system according to a first embodiment of at least one exemplary embodiment.

FIG. 1 illustrates a three-dimensional (3D) image processing system 100 (105 and 220) according to a first embodiment. The 3D image processing system 100 includes a 3D data input device 105 functioning as an object data input device and a 3D data generating device 220 functioning as an object data generating device. The 3D data input device 105 includes a light-emitting unit 110, a turn table 120 functioning as a scanning apparatus, and a composite imaging unit 130 functioning as an imaging apparatus.

The 3D data generating device 220 includes an image processing unit 200 and a shape processing unit 210 that are configured by a computer. The image processing unit 200 constitutes part of a second processing apparatus and the shape processing unit 210 constitutes part of first and second processing apparatuses. Note that although computers are imaged for the processing units 200 and 210 in FIG. 1, a computer is not needed. Any processing units (e.g., Pentium) can be used for the image processing unit 200 and the shape-processing unit 210. Additionally, the function performed in both processors 200 and 210 can be performed in one processor in at least one further exemplary embodiment.

The 3D image processing system 100 according to this embodiment can measure the three-dimensional profile extending horizontally and longitudinally on the surface of an object OBJ and the spectral reflectance of the surface of the object OBJ. Note that although at least one exemplary embodiment refers to "3D", at least one exemplary embodiment can be used for obtaining 2D information (e.g., no rotation of the object). For example the 3D image processing system 100 does not necessarily have to include the turn table 120. If the turn table 120 is not included, the profile of a slit beam (e.g., a sheet beam) incident on the surface of the object OBJ and the spectral reflectance of the illuminated area can be measured. FIG. 1 illustrates the object OBJ for description. However, the object OBJ is not a component of the 3D image processing system according to at least one exemplary embodiment.

Now, the structure of the 3D data input device 105 will be described in detail below. The light-emitting unit 110 emits a slit beam SL (first light beam) to the object OBJ. The slit beam SL is a bundle of light beams that travel within a two-dimensional plane. The slit beam SL can be formed by several methods (e.g., formed by unidirectionally diffusing a linear beam of light at a cylindrical lens or by passing diffused light from a light source through a long, thin rectangular aperture placed in front of the light source). The thickness of the slit beam SL (i.e., width of the line that appears on the surface of the object when the slit beam SL is emitted at the object OBJ) can be selected as desired.

A slit beam can have a significant intensity in the entire spectrum range being measured. The spectrum range of the slit beam SL according to this embodiment is the visible wavelength band. Hence, white light having a uniform intensity in the entire visible wavelength band can be used for the slit beam SL if a visible spectrum range is desired. The spectral intensity distribution of slit beam SL is referred to as $E(\lambda)$.

Figure 2:
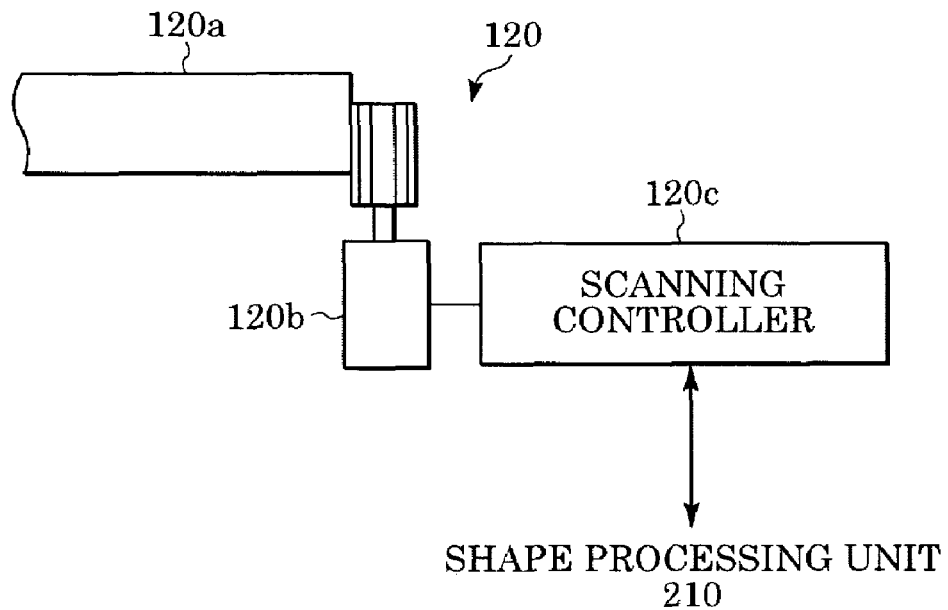
FIG. 2 illustrates the structure of a turn table included in the three-dimensional data processing system according to the first embodiment.
Figure 12:
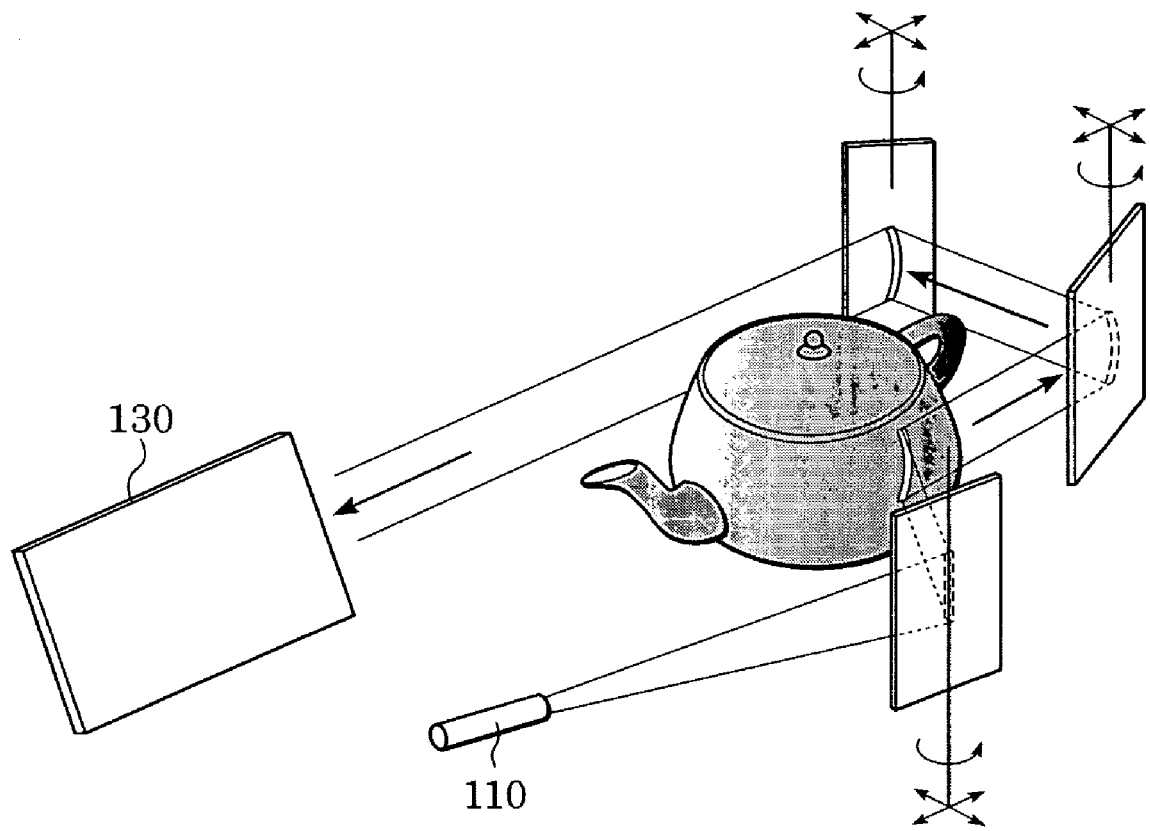
FIG. 12 illustrates the structure of a three-dimensional data processing system according to a variation of a first embodiment of at least one exemplary embodiment.

The turn table 120 according to this embodiment, as illustrated in FIG. 2, includes a table 120a on which the object OBJ is disposed, an actuator 120b, (e.g., a stepping motor), for rotating the table 120a, and a scanning controller 120c for controlling the actuator 120b. The turn table 120 rotates so that the slit beam SL scans the entire surface of the object OBJ. The table 120a rotates in a direction substantially orthogonal to the plane formed by the slit beam SL, i.e., the longitudinal direction of the slit beam SL, so that the slit beam SL efficiently scans the entire surface of the object OBJ. The scanning controller 120c, in at least one exemplary embodiment, is capable of communicating with the shape processing unit 210 and is capable of controlling the actuator 120b in accordance with control signals from the shape processing unit 210. The scanning controller 120c also detects the rotational angle (rotational position) of the table 120a and notifies the shape processing unit 210 of this angle. According to this embodiment, the object OBJ is moved (rotated) relative to the light-emitting unit 110 to scan the surface of object OBJ with the slit beam SL. However, instead, the light-emitting unit 110 may be moved relative to the object OBJ to scan the object OBJ with the slit beam SL. The scanning direction, as described in this embodiment, may be a single direction or, instead, may be a plurality of directions. Furthermore, the object OBJ may be scanned by changing the position and direction of the slit beam SL at the light-emitting unit 110. In other words, any type of the scanning apparatus may be used so long as the slit beam SL and the object OBJ are moved relative to each other. For example, as illustrated in FIG. 12, in at least one further exemplary embodiment the light-emitting unit 110 can rotate and mirrors used to direct the first beam to various portions of the object, where other mirrors direct a portion of the reflected light to the imaging unit 130.

The composite imaging unit 130 according to this embodiment includes an imaging optical system 135, a light-path splitter (optical member) 134, a light section imaging unit 136, and a spectral imaging unit 137. The light section imaging unit 136 includes an image sensor 133. The spectral imaging unit 137 includes a spectrograph 132 and an image sensor 131. The image sensors 131 and 133 may be a CCD sensor and/or a complementary metal oxide semiconductor (CMOS) sensor or any other type of equivalent image sensor or as known by one of ordinary relevant skill in the art.

The light-path splitter 134 splits the light path of the light (i.e., the slit beam SL reflected from the object OBJ) that enters from the imaging optical system 135 such that the light section imaging unit 136 and the spectral imaging unit 137 have the same field of view. Then the light-path splitter 134 guides the light to both the light section imaging unit 136 and the spectral imaging unit 137. The light-path splitter 134 may be a half mirror or a beam splitter or any other type of optical system that redirects a portion of light or splits the light into two or more portions as known by one of ordinary relevant skill in the art.

The imaging optical system 135 can be shared by the light section imaging unit 136 and the spectral imaging unit 137 to form images of the light entering the image sensors 133 and 131 of the imaging units 136 and 137, respectively, via the light-path splitter 134. The irises and the optical axes of the light section imaging system, including the imaging optical system 135 and the light section imaging unit 136, and the spectral imaging system, including the imaging optical system 135 and the spectral imaging unit 137, can be aligned.

The image sensor 133 of the light section imaging unit 136 captures an image formed of the light from the light-path splitter 134. In other words, the image sensor 133 captures the profile of the slit beam SL on the surface of the object OBJ. Alternatively, the image sensor 133 can capture information (e.g., as an image) regarding a shape of an area irradiated with the sheet beam on the surface of the object OBJ. The information regarding the shape includes the shape itself. If the surface of the object OBJ is uneven, the slit beam SL reflected at the surface of the object OBJ represents the profile of the unevenness of the surface of the object OBJ and is captured at the image sensor 133.

The spectrograph 132 separates the light from the light-path splitter 134 based on wavelength and guides the separated light to the image sensor 131 of the spectral imaging unit 137. In other words, the optical system arranged on the light path for the light guided to the image sensor 131 (the light path from the object to the image sensor 131) can have chromatic aberration, and the optical system has a structure such that each color (each wave-length) of the light is separated and entered on different areas of the image sensor 131. In at least one further exemplary embodiment, the chromatic aberration of the optical system arranged on the light path from the object to the image sensor 131 can be larger than at least the chromatic aberration of the optical system arranged on the light path from the object to the image sensor 133. Therefore, an optical element (e.g., a diffraction gating or a prism) can be arranged on the light path from the object to the image sensor 131. The spectral surface of the spectrograph 132 is disposed such that the spectral surface is substantially orthogonal to the plane formed by the light from the light-path splitter 134. In this way, the image sensor 131 can capture a spectral image of the light from the light-path splitter 134, i.e., the slit beam SL reflected from the object OBJ. If the surface of the object OBJ is uneven, the slit beam SL reflected at the surface of the object OBJ will represent this unevenness. Therefore, the spectral image captured by the image sensor 131 will be affected by this unevenness as described below with reference to FIG. 3.

Figure 3:
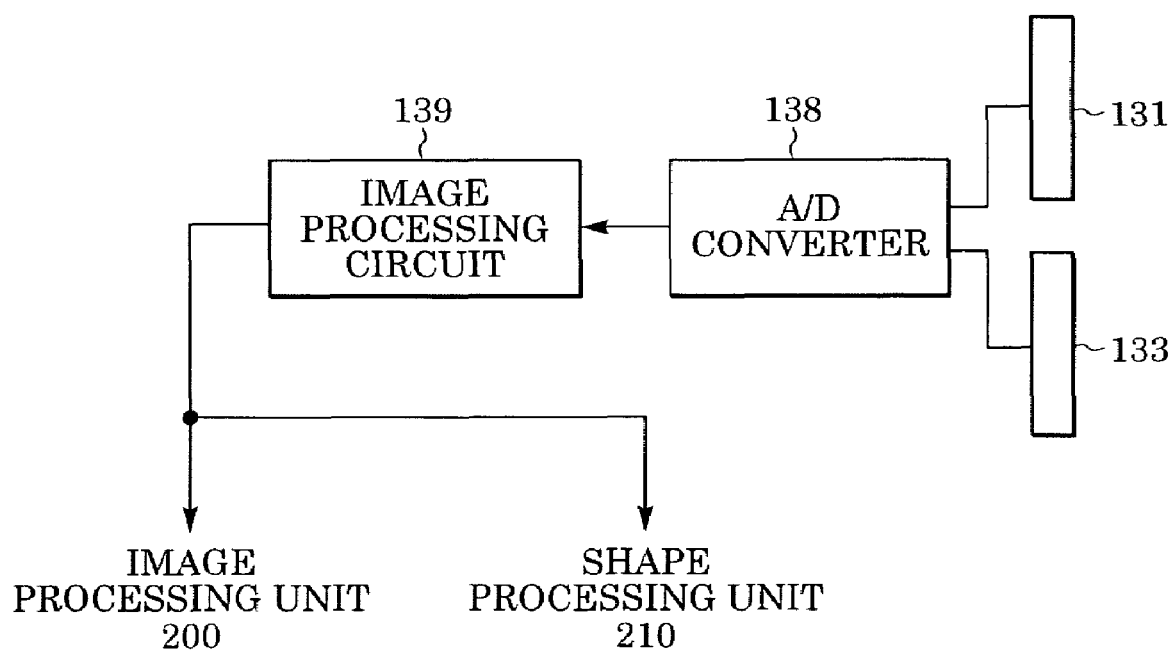
FIG. 3 illustrates the structure of a composite imaging unit included in the three-dimensional data processing system according to the first embodiment.

The output from the image sensors 131 and 133 can be converted from analog to digital by an analog-digital (A/D) converter 138 and input to an image processing circuit 139, as illustrated in FIG. 3. The image processing circuit 139 can generate a light section image (first image) representing the above-mentioned image of the profile of the surface of the object OBJ based on the A/D converted signal sent from the image sensor 133. The image processing circuit 139 also can generates a spectral image (second image) representing the above-mentioned spectral image based on the A/D converted signal output from the image sensor 131. In this embodiment, a light section image and a spectral image are captured each time the turn table 120, i.e., the object OBJ, is rotated by a predetermined angle.

The light section image is sent to the image processing unit 200 and the shape processing unit 210, whereas the spectral image can be sent to the image processing unit 200.

In the description below, the axis of the light section image that is parallel to the plane formed by the slit beam SL is the V axis and the axis parallel to the spectral surface is the U axis. The direction in which the image point on the light section image approaches U=0 is defined as the reference direction. The U' coordinate value u', representing the imaging position on the spectral image, of light having a wavelength λ entering from the reference direction is defined as u'=spectr(λ).

The image processing unit 200 receives the light section image and the spectral image from the composite imaging unit 130 and then carries out calibration based on the light section image to relate positions on the spectral image surface to spectral wavelengths. From the calibrated spectral image, the image processing unit 200 calculates the spectral intensity of the received light to calculate the spectral reflectance of each region of the object OBJ irradiated with the slit beam SL (each of these regions is referred to as a "section line," as described below). The data of the spectral intensity of the received light can be output to the shape processing unit 210. Details of the processing carried out at the image processing unit 200 and the shape processing unit 210 are described below.

The shape processing unit 210 calculates the shape (cross-sectional shape) of the object OBJ in the region irradiated with the slit beam SL based on the light section image sent from the composite imaging unit 130 and the positional data indicating the relative positional relationship between the light-emitting unit 110, the object OBJ and the composite imaging unit 130. The positional data is stored in advanced in a memory (not shown in the drawings) in the shape processing unit 210, although it can be stored in other locations. The shape processing unit 210 uses the light section images obtained at each rotational position of the object OBJ to finally calculate the three-dimensional shape of the entire object OBJ.

The shape processing unit 210 can also calculate the spectral reflectance (spectral data) of each region of the object OBJ irradiated with the slit beam SL based on the spectral intensity of the received light sent from the image processing unit 200. The shape processing unit 210 uses the spectral images obtained at each rotational position of the object OBJ to finally calculate the spectral reflectance of the entire surface of the object OBJ.

The shape processing unit 210 relates the data indicating the three-dimensional shape of the object OBJ and the spectral reflectance of the entire surface of the object OBJ and outputs or records the results. Details of the processing carried out by the shape processing unit 210 are described below.

In this embodiment, the image processing unit 200 and the shape processing unit 210 are described as separate units. However, the functions of these units may be realized by a single computer system. In such a case, the functions of the image processing unit 200 and the shape processing unit 210 may also be realized as a series of computer programs.

Now, operations of the 3D image processing system 100 will be described in detail below. The acquisition of the light section image and the spectral image will be described with reference to the flow chart in FIG. 4. This operation can be controlled by the shape processing unit 210 or the image processing unit 200.

As illustrated in FIG. 1, the operator carrying out the measurement disposes the object OBJ on the turn table 120 and turns on the measurement start switch (not shown in the drawings). The light-emitting unit 110 is turned on to emit the white slit beam SL onto the object OBJ (Step S1). As a result, a bright section line C appears on the surface of the object OBJ irradiated with the slit beam SL. The composite imaging unit 130 is disposed a predetermined distance away from the object OBJ such that the section line C is included within the imaging field of view. At this point, the relationship between the position and orientation of the turn table 120 and the position and orientation of the composite imaging unit 130 is determined, and positional data representing this relationship is sent to a processing unit (e.g., the shape processing unit 210).

Next, the turn table 120 is rotated to an initial position (Step S2). Then, the light section image and the spectral image of the object OBJ are captured by the composite imaging unit 130 (Step S3). The obtained light section image and spectral image can be output to the image processing unit 200 and the shape processing unit 210 (Step S4). Next, it is determined whether or not the captured images are the last images to be captured in an image capturing process of the entire object OBJ (Step S5). If the captured images are the last images to be captured, the process is ended. If the captured images are not the last images to be captured, the turn table 120 is rotated by a predetermined angle (Step S6) and the process is returned to Step S3 to capture subsequence images. In this way, a light section image and a spectral image are captured every time the turn table 120 is turned by a predetermined angle. The captured light section images and spectral images can be output in sequence to the image processing unit 200 and the shape processing unit 210.

In this embodiment, the light section image and the spectral image are captured simultaneously by splitting the slit beam SL reflected at the object OBJ by the light-path splitter 134. In other words, a light section image and a spectral image are obtained from a single slit beam. More specifically, a light section image and a spectral image of the same region (same rotational position) on the surface of the object OBJ is obtained.

Figure 5A:
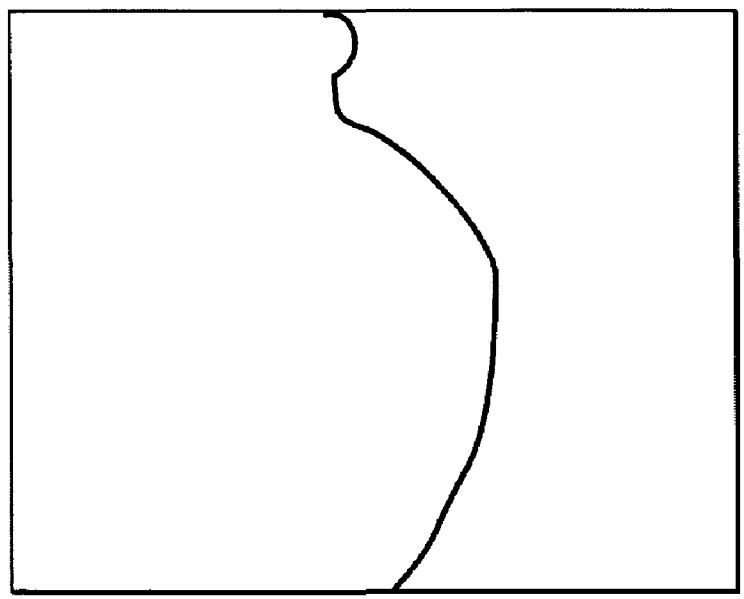
FIG. 5A illustrates an example of a light section image.
Figure 5B:
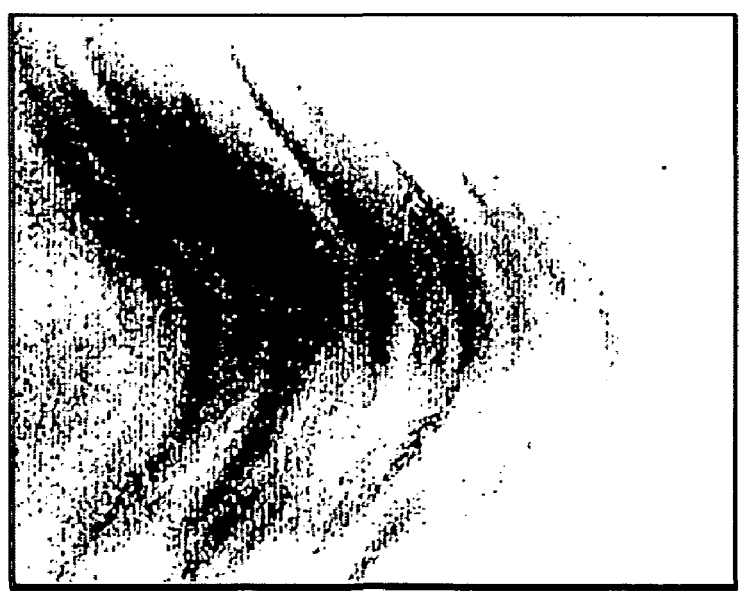
FIG. 5B illustrates an example of a spectral image.

FIGS. 5A and 5B illustrate examples of a light section image and a spectral image, respectively. In the drawings, the vertical axis is the V axis and the horizontal axis is the U axis. In FIG. 5A, illustrating the light section image, an image of the section line C that appeared on the surface of the object OBJ irradiated with the slit beam SL is shown as a single line. Since the composite imaging unit 130 captures an image at an angle relative to the direction of the slit beam SL emitted towards the object OBJ, the image of the section line C represents the profile of the surface of the object OBJ. The spectral image is an image of the section line spectrally separated in the direction of the U axis.

For a typical image spectrograph, the U' coordinate value and the spectral wavelength of the spectral image directly correspond to each other. However, for the system according to this embodiment, the incident angle of light to the spectrograph 132 does not have to be fixed since the incident direction to the spectral imaging system depends on the position of the section line C that changes in accordance with the shape of the object OBJ. Therefore, the U coordinate value and the spectral wavelength of the spectral image do not directly correspond to each other.

The light section image and the spectral image captured at the same rotational position can be output as a pair to the image processing unit 200. The light section image is sent to the shape processing unit 210 together with the rotational position of the turn table 120.

The image processing unit 200 calculates the spectral intensity of the light reflected at the section line C based on the light section image and the spectral image input from the composite imaging unit 130. The operation of the image processing unit 200 is shown in the flow chart in FIG. 6.

Figure 6:
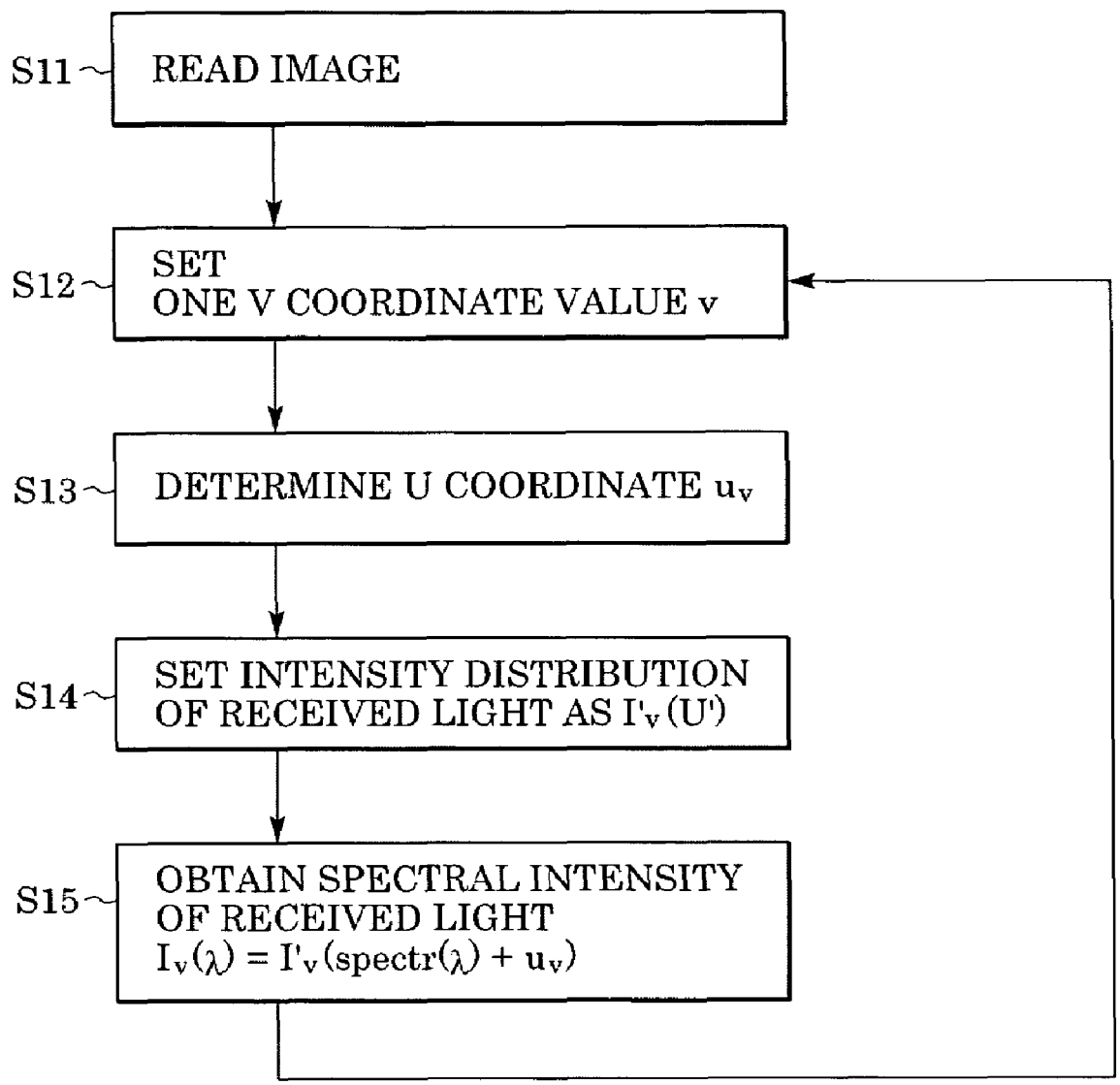
FIG. 6 is a flow chart illustrating the operation of a three-dimensional data generating device included in the three-dimensional data processing system according to the first embodiment.

According to FIG. 6, the image processing unit 200 reads the light section image and spectral image sent from the composite imaging unit 130 (Step S11).

The image processing unit 200 sets a V coordinate value v in sequence within the V coordinate region of the light section image including the image of the section line C. In other words, the image processing unit 200 divides the V coordinate region of the light section image including the image of the section line C from the minimum V coordinate value to the maximum V coordinate value into predetermined increments and, in sequence, sets each increment as the V coordinate value v (Step S12). Then the image processing unit 200 carries out the processing described below.

Figure 7:
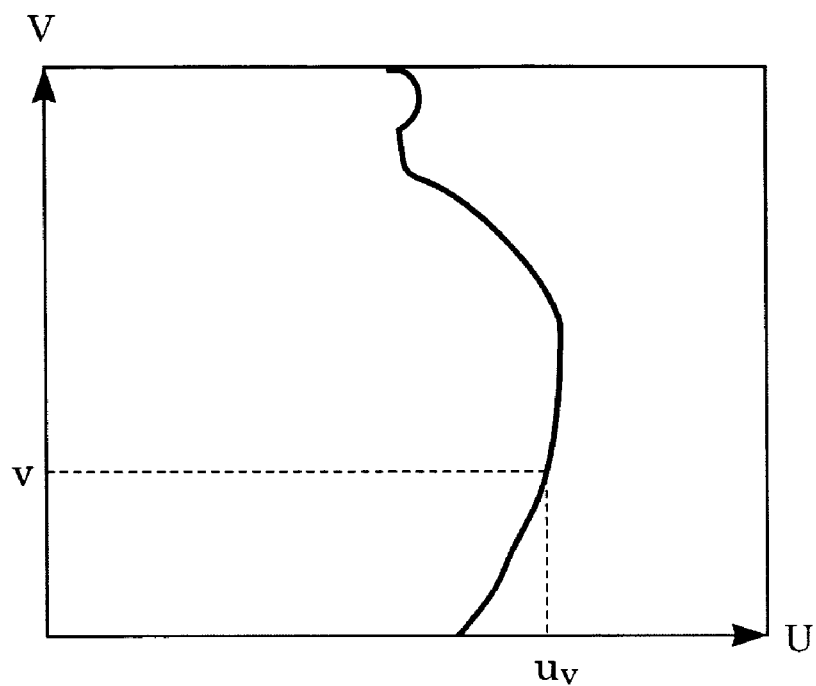
FIG. 7 illustrates $u_v$.

The image processing unit 200 determines the U coordinate $u_v$ where the V coordinate equals v on the section line C, as illustrated in FIG. 7 (Step S13).

Figure 8:
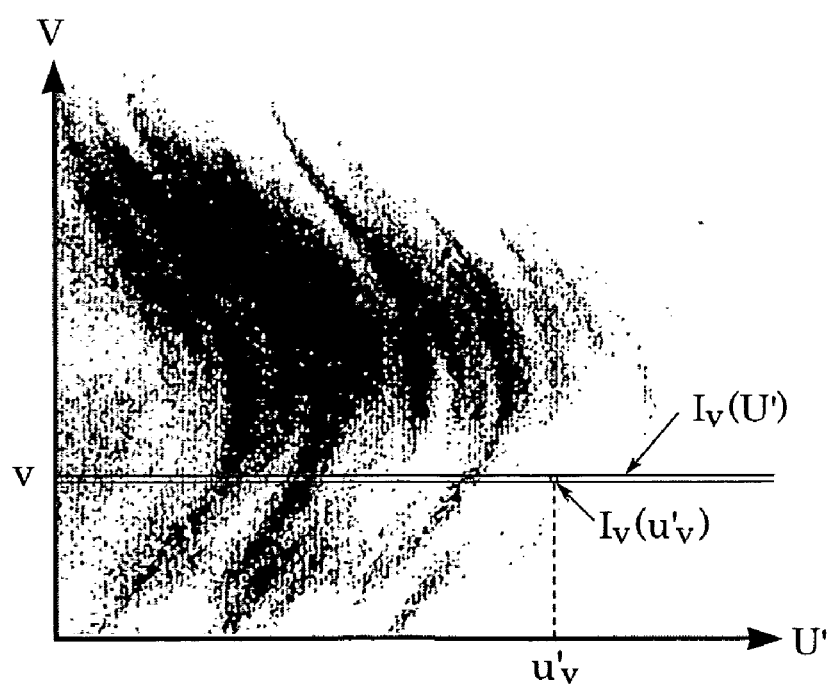
FIG. 8 illustrates $I_v(U)$.

As illustrated in FIG. 8, the intensity distribution of the line V=v on the spectral image is defined as $I'_v(U')$ (Step S14).

The spectral intensity of the region where the V coordinate on the light section image equals v, i.e., $I_v(\lambda)=I'_v(\text{spectr}(\lambda)+u_v)$, is determined (Step S15). This processing is repeated for each v. As a result, the spectral intensity of all regions of the section line C irradiated with the slit beam SL is determined.

Figure 9:
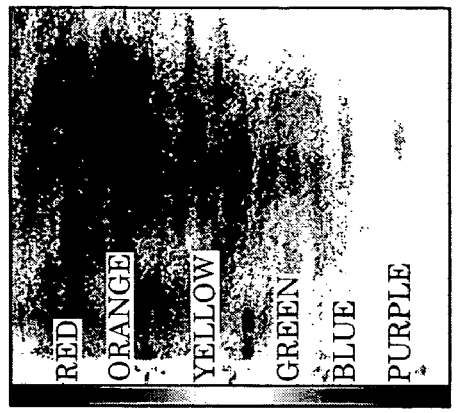
FIG. 9 illustrates an example of a calibrated spectral image.

If the direct relationship between the wavelength λ of the above-mentioned $I_v(\lambda)$ to the U' coordinate is plotted, an image equivalent to a spectral image obtained using a typical imaging spectrograph can be obtained (FIG. 9).

The shape processing unit 210 calculates the profile of the section line C on the object OBJ (i.e., shape of the region on the surface of the object OBJ where the section line C is present) from the light section image sent from the composite imaging unit 130. This calculation may be performed by several methods (e.g., light section method, where an example of the light section method is described in "Three-dimensional Image Measurement (san jigen gazou keisoku)" (Shokodo Co. Ltd.: 1990) by Seiji Inokushi and Kosuke Sato).

The shape processing unit 210 converts the spectral intensity data from the image processing unit 200 into spectral reflectance data.

More specifically, the spectral reflectance at a measuring point t is determined by the following formula:

$$R_t(\lambda)=_{att}(l_{light})/l_{OBJ}^2 \times I_t(\lambda)/(E(\lambda)S(\lambda)T(\lambda))$$

where, T is the point on the surface of the object OBJ corresponding to the measurement point t (e.g., FIG. 1) determined based on the positional relationship between the object OBJ, the light-emitting unit 110, and the composite imaging unit 130 at when the spectral image used for calculating the spectral intensity $I_t(\lambda)$ of the received light, $l_{light}$ is the distance between the point T and the light-emitting unit 110, $l_{OBJ}$ is the distance between the point T and the composite imaging unit 130, E(λ) is the spectral of the light emitted from the light-emitting unit 110, S(λ) is the spectral sensitivity of the image sensor 131, and T(λ) is the spectral transmittance of the imaging optical system 135, the light-path splitter (half mirror, or polarization beam splitter) 134, and the spectrograph 132. Moreover, $_{att}(l)$ is a damping function of a slit beam (sheet beam) and for light that is diffused in a fan-like form $_{att}(l)=l^{-1}$.

Even if the individual values of E(λ), S(λ), and T(λ) are unknown, the product (E(λ)S(λ)T(λ)) can be obtained by measuring an object having a known spectral reflectance $R_{carib}(\lambda)$, obtaining the spectral intensity $I_{carib}(\lambda)$ of the received light, and then applying these values to the formula below:

$$E(\lambda)S(\lambda)T(\lambda)=_{att}(l_{light})/l_{OBJ}^2 \times I_{carib}(\lambda)/R_{carib}(\lambda)$$

As described above, the shape and the spectral reflectance of the region corresponding to the section line C on the surface of the object OBJ are obtained. By repeatedly carrying out the above-described process on the plurality of pairs of a light section image and a spectral image obtained at each rotational position of the object OBJ, the overall three-dimensional shape of the object OBJ and the spectral reflectance of the entire surface of the object OBJ are obtained.

The three-dimensional shape of the object OBJ and the spectral reflectance of the entire surface of the object OBJ obtained according to the above-described process are input to a computer graphics (CG) apparatus 500. The PG apparatus 500 reconstructs an image representing the three-dimensional shape and the spectral reflectance of the object OBJ. Other exemplary embodiments can have a similar reconstruction process.

In accordance with at least one exemplary embodiment, a beam SL (e.g., one slit beam) can be incident at the object OBJ. However, in yet other exemplary embodiments, a plurality of slit beams may be emitted at the object. In such a case, the image processing unit 200 and the shape processing unit 210 can carry out the above-described process for a plurality of section lines captured by the light section image and the spectral image.

Second Embodiment

Figure 10:
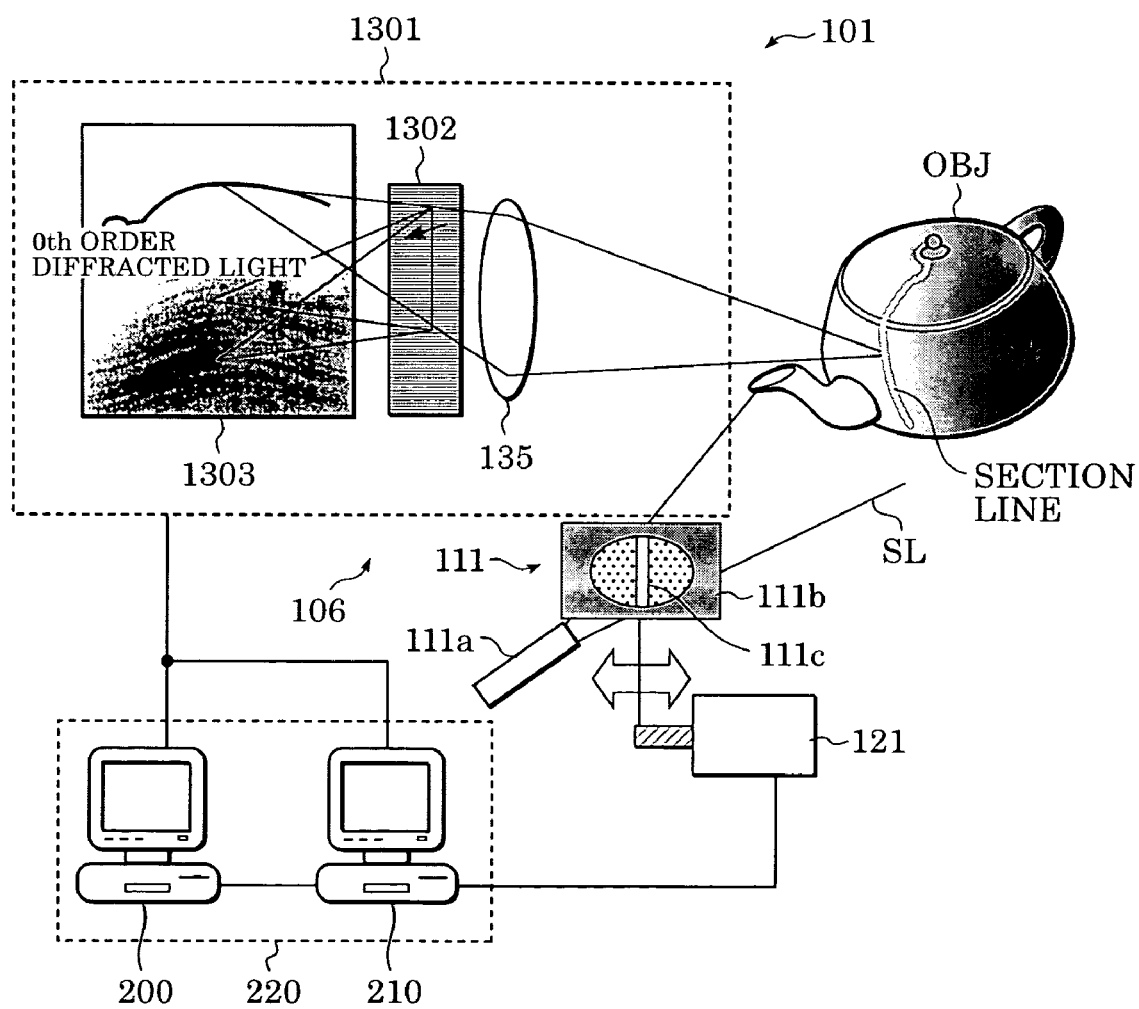
FIG. 10 illustrates the structure of a three-dimensional data processing system according to a second embodiment of at least one further exemplary embodiment.

FIG. 10 illustrates a three-dimensional (3D) image processing system 101 according to a second embodiment of at least one exemplary embodiment. The 3D image processing system 101 includes a 3D data input device 106 that is an object data input device (e.g., 111 and 1301) and a 3D data generating device 220 that is an object data generating device. The 3D data input device 106 includes a light-emitting unit 111, a scanning unit 121, and a composite imaging unit 1301 functioning as an imaging apparatus.

The 3D data generating device 220 includes an image processing unit 200 constituting part of a second processing apparatus and a shape processing unit 210 constituting part of first and second processing apparatus. In at least one exemplary embodiment, the image processing unit 200 and shape processing unit 210 can both be configured by a computer.

The light-emitting unit 111 includes a light source 111a for emitting diffused light and an aperture panel 111b having a thin aperture 111c extending in the longitudinal direction and being disposed in front of the light source 111*a*. Light from the light source 111*a* that passes through the aperture 111*c* is emitting onto an object OBJ as a slit beam SL. The slit beam SL can be a white light beam having an intensity distribution $E(\lambda)$ similar as the slit beam according to the first embodiment.

The scanning unit 121 can includes an actuator and a scanning controller for controlling the actuator and drives the aperture panel 111*b* in a direction substantially orthogonal to the longitudinal (vertical) direction of the aperture 111*c*, i.e., the aperture panel 111*b* is moved in the horizontal direction. In this way, the slit beam SL that passes through the aperture 111*c* also moves in the horizontal direction. The scanning unit 121, in at least one exemplary embodiment, is capable of communicating with the shape processing unit 210 and is capable of notifying the position of the aperture panel 111*b* to the shape processing unit 210.

In at least one exemplary embodiment, the light-emitting unit 111 may be any type of multiple frequency emitter(s) (e.g., an image projector including a liquid crystal panel and micromirror array). In such a case, the slit beam SL will be projected on the object OBJ by projecting an image including a single while straight line to the object OBJ. The scanning of this type of slit beam SL will be performed by the scanning unit 121 by projecting images including straight lines in different positions on the object OBJ in sequence.

The composite imaging unit 1301 includes an imaging optical system 135, a diffracting element 1302 including a diffraction grating, and an image sensor 1303. The diffracting element 1302 splits the light path of the light entering the composite imaging unit 1301, i.e., the light reflected from the object OBJ, into two paths by diffraction. More specifically, the diffracting element 1302 splits the light into a non-diffracted light beam (0th order light) and a diffracted light beam (for example, 1st order light) propagating at an angle relative to the non-diffracted light beam. The diffracting plane of the diffracting element 1302 is disposed such that the plane is substantially orthogonal to the plane formed by the incident slit beam SL.

The image sensor 1303 includes a light-receiving area for capturing an image representing the profile of the non-diffracted light beam from the diffracting element 1302, i.e., an image of the profile of the slit beam SL on the surface of the object OBJ, and another light-receiving area for capturing a spectral image of the diffracted light beam, i.e., an image representing the spectrum of the slit beam SL reflected at the surface of the object OBJ. In this embodiment, the non-diffracted light beam and the diffracted light beam is received in different light-receiving areas by the same image sensor. However, in other exemplary embodiments, the non-diffracted light beam and the diffracted light beam may be received by separate image sensors.

The composite imaging unit 1301 carries out a process that is the same as the process according to the first embodiment illustrated in FIG. 3 to the outputs from the light-receiving areas of the image sensor 1303 to generate a single image including both a light section image based on the non-diffracted light beam and a spectral image based on the diffracted light beam. Then the composite imaging unit 1301 sends this image to the image processing unit 200 and the shape processing unit 210.

Figure 4:
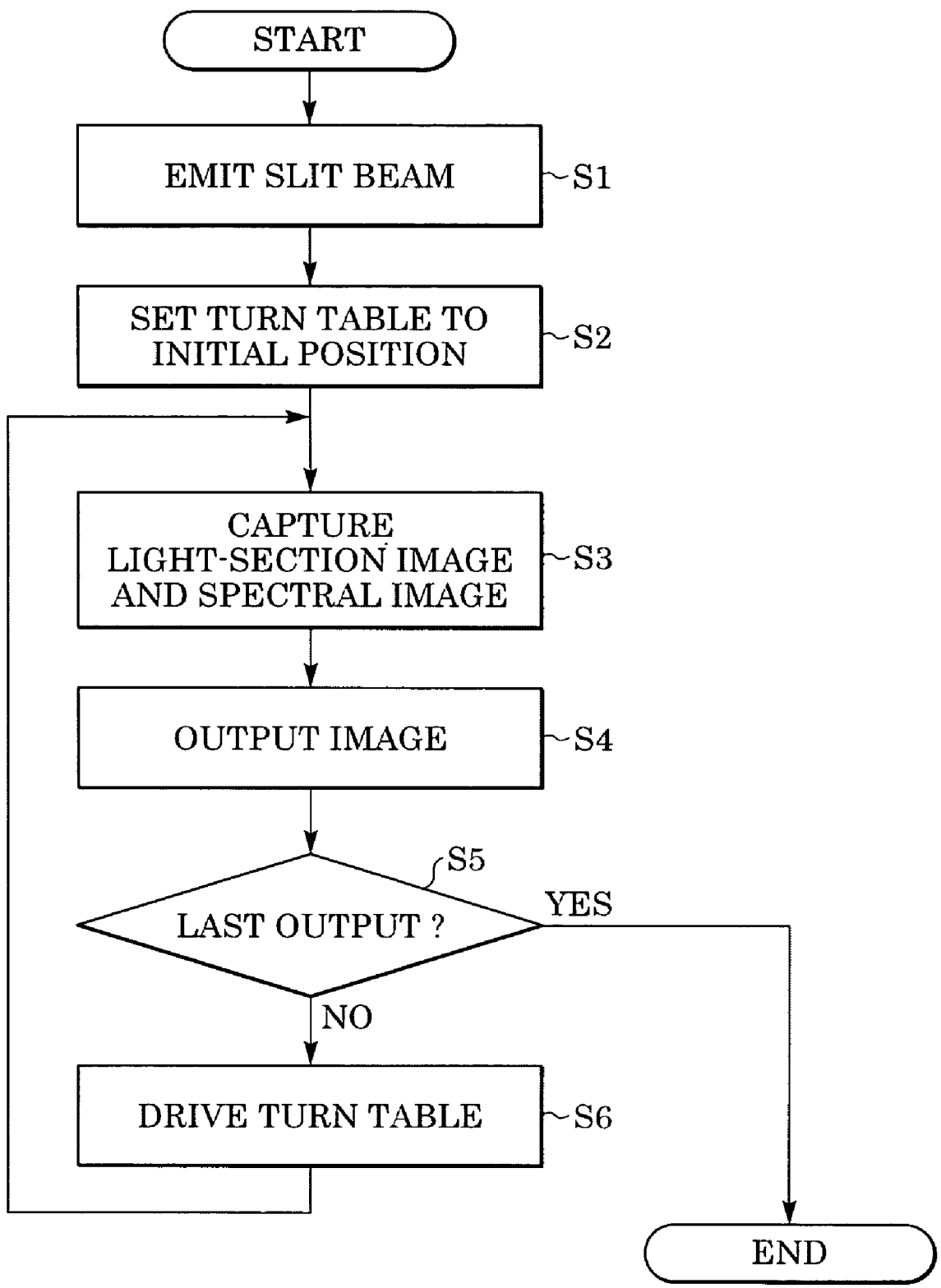
FIG. 4 is a flow chart illustrating the operation of a three-dimensional data input device included in the three-dimensional data processing system according to the first embodiment.

The acquisition process of the light section image and the spectral image is the same as the process according to the first embodiment, as illustrated in FIG. 4, except that in Step S2 the scanning unit 121 is set to an initial position and in Step S6 the scanning unit 121 is driven to the subsequent position.

The image processing unit 200 and the shape processing unit 210 calculate the three-dimensional shape of the object OBJ and the spectral reflectance of the surface of the object OBJ, respectively, by the same processes as described in the first embodiment.

According to this embodiment, the diffracting element 1302 is used instead of the light-path splitter 134 and the spectrograph 132 according to the first embodiment. Since light section images and spectral images are both captured by a single image sensor 1303, the composite imaging unit 1301 can be structured with fewer components and in a smaller size compared to the composite imaging unit 130 according to the first embodiment.

The light-emitting unit 111 according to this embodiment may also be used for the first embodiment.

Third Embodiment

Figure 11:
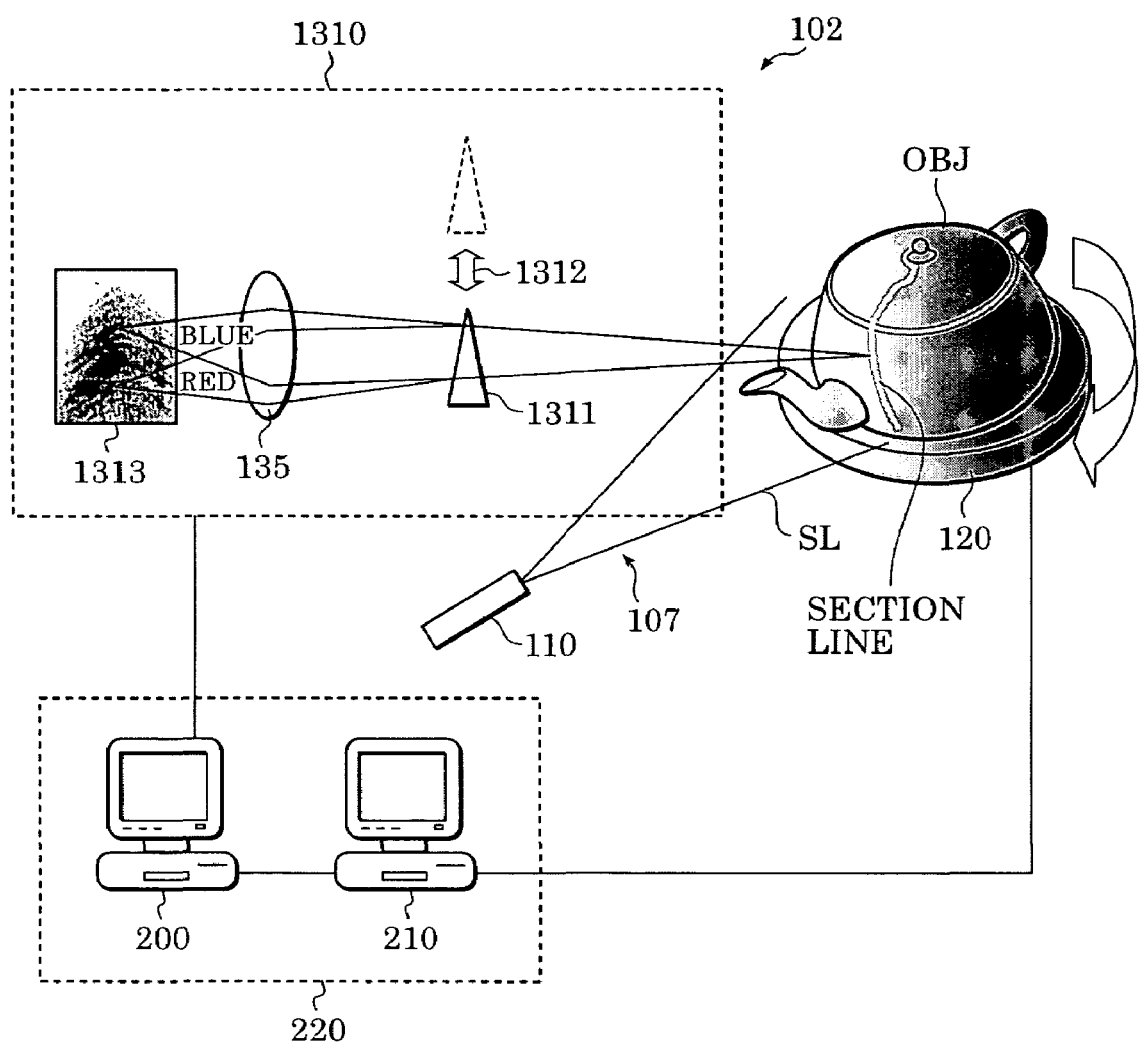
FIG. 11 illustrates the structure of a three-dimensional data processing system according to a third embodiment of at least one further exemplary embodiment.

FIG. 11 illustrates a three-dimensional (3D) image processing system 102 according to a third embodiment of at least one exemplary embodiment. The 3D image processing system 102 includes a 3D data input device 107 that is an object data input device and a 3D data generating device 220 that is an object data generating device. The 3D data input device 107 includes a light-emitting unit 110, a turn table 120, and a composite imaging unit 1310 functioning as an imaging apparatus.

The 3D data generating device 220 can include an image processing unit 200 constituting part of a second processing apparatus and a shape processing unit 210 constituting part of first and second processing apparatuses. In at least one exemplary embodiment, the image processing unit 200 and shape processing unit 210 are both configured by a computer.

The composite imaging unit 1310 according to this embodiment includes an imaging optical system 135, a spectrograph 1311, a spectrograph attachment mechanism 1312, and an image sensor 1313.

The spectrograph attachment mechanism 1312 is a mechanism for moving the spectrograph 1311 into and out of the light path (imaging light path) of the slit beam SL that is emitted from the light-emitting unit 110 to the object OBJ, reflected off the object OBJ, and entered into the imaging optical system 135. The spectrograph 1311 spectrally separates the incident light according to wavelength in the same way as the spectrograph according to the first embodiment. By disposing the spectrograph 1311 in the imaging light path, a spectral image of the reflected slit beam SL is formed on the image sensor 1313. By moving the spectrograph 1311 out from the imaging light path, an image representing the shape of the reflected slit beam SL (the profile of the slit beam SL on the object OBJ) is formed on the image sensor 1313. Accordingly, by moving the spectrograph 1311 into and out from of the imaging light path, the composite imaging unit 1310 captures light section images and spectral images in series. These images are sent to the image processing unit 200 and the shape processing unit 210.

The spectrograph 1311 according to this embodiment can be of a so-called rectilinear type in which the field of view does not changed when moved into and out from the light path (e.g., a grism spectrograph).

According to this embodiment, a camera module having the image sensor 1313 and the imaging optical system 135 can be used as a composite imaging unit by just adding the spectrograph 1311 and the spectrograph attachment mechanism 1312.

The structures and operations of the light-emitting unit 110, turn table 120, image processing unit 200, and the shape processing unit 210 according to this embodiment are the same as those according to the first embodiment.

The composite imaging unit 1310 according to this embodiment cannot simultaneously capture a light section image and a spectral image. Therefore, for the shape processing unit 210 to capture a light section image and a spectral image, the turn table 120 can be at substantially the same position while capturing each image or, instead, the light section images (or the spectral images) of the entire object OBJ are captured and then the spectral images (or the light section images) of the entire object OBJ are captured. In other words, the operation according to Step S3 in FIG. 4 will include capturing the light section images, then moving the spectrograph 1311 into the light path, then capturing the spectral images, and finally moving the spectrograph 1311 out from the light path.

The composite imaging unit 1310 according to this embodiment may also be used for the system according to the second embodiment.

Summary

The descriptions of the exemplary embodiments are summarized below.

The composite imaging unit according to at least one exemplary embodiment emits a slit beam to an object and captures a light section image representing the profile of the slit beam on the surface of the object and a spectral image representing the spectrum of the slit beam reflected at the surface of the object. In this way, the shape and the spectral reflectance of a line on the surface of the object irradiated with a slit beam is measured.

The scanning apparatus according to at least one exemplary embodiment is capable of changing the position and/or the orientation of at least one of the object and the light-emitting unit. In this way, at least a portion of the areas on the surface of the object extending vertically and horizontally, irradiated with a slit beam, is scanned.

The scanning apparatus in at least one exemplary embodiment can be used as a mechanism for emitting a white slit beam on as much of the surface of the object as possible in sequence. In at least one exemplary embodiment, one of the axes of the moving part of the mechanism moves or rotates the object within a plane substantially orthogonal to the plane formed by the slit beam. In at least one exemplary embodiment, the slit beam should have a significant intensity in the entire spectral range to be measured such that scattered reflections of the slit beam from the object are detectable on the spectral image. In at least one exemplary embodiment, white light for the slit beam can be used when measuring the spectrum of a visible wavelength band.

Ideally, although not needed for exemplary embodiments to operate, the spectral intensity distribution of the slit beam should not change irregularly during measurement, and the spectral intensity distribution, the spectral sensitivity of the image sensor, and the spectral transmittance of the optical system should be known. It is also possible to measure the spectral intensity distribution, the spectral sensitivity of the image sensor, and the spectral transmittance of the optical system before or after measuring the object. In particular, it is common to perform calibration for known spectral measurement apparatus by measuring an object having a known spectral reflectance. This method of calibration can be suitably applied to the apparatus in accordance with at least one exemplary embodiment.

In accordance with the scanning operation, the composite imaging unit captures a plurality of the light section images and spectral images in which the positional relationship between the slit beam and the object differ. The spatial resolution increases as the number of captured images increase. The more constant the differences in the positional relationship between the slit beam and the object for each captured image, the more uniform the obtained data. In at least one exemplary embodiment an improved spatial resolution and more uniform data, the composite imaging unit can capture a light section image and a spectral image in predetermined intervals.

In at least one exemplary embodiment, the composite imaging unit can capture a light section image in the same position as the spectral image by using the same slit beam used for the spectral image. In this way, the captured light section image will represent the same positional relationship between the slit beam (sheet beam) and the object as the relationship between the slit beam (sheet beam) and the object represented by the spectral images. In other words, a light section image and a spectral image may be captured simultaneously.

The composite imaging unit can capture the shape and a spectral image of the slit beam emitted on the surface of an object as a light section image and a spectral image. The composite imaging unit, in at least one exemplary embodiment, is capable of capturing such light section images and spectral images by including a light section imaging system for capturing light section images and a spectral imaging system for capturing spectral images.

The spectral imaging system can include a two-dimensional imaging device and a spectrograph. The spectral plane of the spectral imaging system, ideally although not necessarily, should not be parallel with the plane formed by the slit beam and, in at least one exemplary embodiment, the spectral plane of the spectral imaging system can be substantially orthogonal to the plane formed by the slit beam.

A light-path splitter can be disposed in front of the light section imaging system and the spectral imaging system to split the slit beam reflected at the surface of the object and to guide the split slit beam to both the light section imaging system and the spectral imaging system. In this way, the light section imaging system and the spectral imaging system can have the same field of view. In at least one exemplary embodiment, the light section imaging system and the spectral imaging system can be disposed so that their optical axes substantially match through the light-path splitter.

The light-path splitter facilitates the sharing of part or all of the imaging optical system by the light section imaging system and the spectral imaging system. For the light section imaging system and the spectral imaging system to share part of or all of the imaging optical system, the light-path splitter should be disposed inside or behind (on the image sensor side) of the imaging optical system.

Alternatively, for the light section imaging system and the spectral imaging system to share part of or all of the imaging optical system, a diffracting element may be included in the composite imaging unit so that light section images are captured by the straight light and spectral images are captured by the diffracted light. In this case, the light-path splitter and the spectrograph included in the above-described composite imaging unit are replaced with a diffraction grating. To separate the straight light and the diffracted light, the diffracting plane of the diffracting element can be disposed substantially orthogonally with the plane formed by the slit beam. Thus, at least one exemplary embodiment can use one imaging optical system.

Another composite imaging unit may include a spectrograph capable of moving into and out from the imaging light path. In at least one exemplary embodiment, a rectilinear type spectrograph can be used, which does not substantially change its field of view when moved into and out of the imaging light path.

In case of a known imaging spectrograph, the incident angle of light entering the spectrograph is limited by the linear slit disposed in front of the spectrograph. Therefore, the positions on an image surface directly correspond to the spectral wavelengths. According to at least one exemplary embodiment, the incident direction of light depends on the section line formed on the object by a slit beam and changes as the section line changes along the surface of the object. Accordingly, the relationship between the positions on the surface of the spectral image and the spectral wavelengths is calibrated based on the incident direction obtained from a light section image formed by capturing light that has not passed through the spectrograph and from a spectral image formed by capturing light that has passed through the spectrograph. By performing this calibration at the image processing unit, the spectral intensity of the received light can be obtained from the spectral image.

At a shape processing unit, the spectral reflectance can be obtained by measuring the three-dimensional shape of the object based on the light section images and by taking into account the positional relationship of the object the light-emitting unit, and the composite imaging unit of when the spectral image corresponding to the spectral intensity was captured. According to at least one exemplary embodiment, the spectral intensity of the received light is measured in a two-dimensional spatial distribution corresponding to a wide range on the surface of the object extending in the longitudinal direction of the section line formed by the slit beam and in the direction the slit beam is scanned by a scanning apparatus. The spectral reflectance of the three-dimensional surface of the object is related to the three-dimensional shape of the object and then can be outputted and recorded.

By applying the object data input device and the method for inputting object data according to at least one exemplary embodiment, images, which can be used for obtaining the shape and the spectral data of the object, can be obtained by using the same light beam (first light beam) emitted onto the object.

By applying the object data generating device and the method for inputting object data according to at least one exemplary embodiment, the shape and the spectral data of the object can be obtained based on images representing the shape and images representing the spectra of the object by using the same light beam (first light beam) emitted onto the object.

While the present invention has been described with reference to exemplary embodiments, it is to be understood that the invention is not limited to the disclosed embodiments. On the contrary, the invention is intended to cover various modifications and equivalent arrangements included within the spirit and scope of the appended claims, specification, drawings, and as known by one of ordinary relevant skill in the art. The scope of the following claims is to be accorded the broadest interpretation so as to encompass all such modifications and equivalent structures and functions.

This application claims priority from Japanese Patent Application No. 2004-176200 filed Jun. 14, 2004, which is hereby incorporated herein in its entirety.

What is claimed is:

1. An object information generating apparatus comprising:
    a first processing unit configured to generate a shape of the object based, wherein the first processing unit is configured to use a first set of data that includes at least one characteristic of a first portion of light reflected from the object; and
    a second processing unit configured to generate spectral data, wherein the second processing unit is configured to use a second set of data that includes at least one characteristic of a second portion of light reflected from the object, wherein the at least one characteristic of a second portion of light reflected from the object includes information from a first and second image.

2. The object information generating apparatus according to claim 1, wherein the second processing unit calibrates the relationship between regions on the second image and spectral wavelengths based on the first image and generates the spectral data based on the results of the calibration.

3. The object information generating apparatus according to claim 1, wherein the at least one characteristic of a first portion of light reflected from the object includes information from the first image, wherein the first processing unit calculates the three-dimensional shape of the object based on the information from the first image, and wherein the second processing unit generates spectral data corresponding to the three-dimensional shape of the object based on the information from the first image and the second image.

4. An object data processing system, comprising: a light emitting unit configured to emit a first light beam to an object; an imaging unit configured to acquire a first image representing a shape of an area on the surface of the object and a second image representing a spectrum of a portion of the first light beam reflected from the surface of the object; a first processing unit configured to generate a shape of the object based on the first image; and a second processing unit configured to generate spectral data based on the first image and the second image, wherein the spectral data also corresponds to the shape of the object.

* * * * *